(12) United States Patent
Takamatsu et al.

(10) Patent No.: US 6,500,946 B1
(45) Date of Patent: *Dec. 31, 2002

(54) METHODS FOR PRODUCING NUCLEOSIDE DERIVATIVES AND INTERMEDIATES THEREFOR

(75) Inventors: Satoshi Takamatsu; Satoshi Katayama; Naoko Hirose; Kunisuke Izawa, all of Kawasaki; Tokumi Maruyama, Tokushima, all of (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/567,980

(22) Filed: May 10, 2000

Related U.S. Application Data

(63) Continuation of application No. 09/267,789, filed on Mar. 15, 1999, now Pat. No. 6,090,937.

(30) Foreign Application Priority Data

Mar. 17, 1998 (JP) ............................................. 10-088163

(51) Int. Cl.[7] ............................................. C07H 19/19

(52) U.S. Cl. ............................... 536/27.11; 536/27.14; 536/27.21; 536/27.4; 536/27.62; 536/27.8

(58) Field of Search ..................... 536/27.11, 27.14, 536/27.21, 27.4, 27.62, 27.8

(56) References Cited

U.S. PATENT DOCUMENTS

| | | | |
|---|---|---|---|
| 5,144,018 A | 9/1992 | Kuzuhara et al. | 536/27.14 |
| 5,290,927 A | 3/1994 | Honda et al. | 536/27.6 |
| 5,310,895 A | 5/1994 | Shiragami et al. | 536/27.14 |
| 5,451,671 A | 9/1995 | Shiragami et al. | 536/27.12 |
| 5,466,793 A | 11/1995 | Honda et al. | 536/55.3 |
| 5,476,931 A | 12/1995 | Kuzuhara et al. | 536/55.3 |
| 5,625,057 A | 4/1997 | Shiragami et al. | 536/55.3 |
| 5,633,366 A | 5/1997 | Takamatsu et al. | 536/28.4 |
| 5,760,255 A * | 6/1998 | Vorbrüggen et al. | 552/502 |
| 6,090,937 A * | 7/2000 | Takamatsu et al. | 536/27.11 |

FOREIGN PATENT DOCUMENTS

| | | | |
|---|---|---|---|
| CA | 1189069 | * | 6/1985 |
| EP | 0 311 694 | | 4/1989 |
| WO | 8808427 | * | 11/1988 |

OTHER PUBLICATIONS

Kawana et al. (I), "General Method for the Synthesis of 2'–Azido–2', 3'–dideoxynucleosides by the Use of [1,2] –Hydride Shift and β–Elimination Reactions," *Journal of the Chemical Society, Perkin Transactions I*, 1992, No. 4, 469–478 (Feb. 1992).*

Kawana et al. (II), "Facile Transformation of β–D–Ribofuranosyl Purines and Pyrimidines Into Their Respective 3'–Deoxy–threo–pentofuranosyl Nucleosides," *Journal of the Chemical Society, Perkin Transactions I*, 1989, No. 9, 1593–1596 (Sep. 1989).*

Mengel et al., "Umwandlung von Inosin in 2'– und 3'–Desoxy–Sowie 2', 3'–Anhydroinosin," *Justus Liebig's Annalen de Chemie*, 1977(10), 1585–1596 (Oct., 1977).*

Middleton, "New Fluorinating Reagents. Dialkylaminosulfur Fluorides," *Journal of Organic Chemistry*, 45(5), 574–578 (1975).*

Bennua–Skalmowski et al., A Facile Conversion of Primary or Secondary Alcohols with n–Perfluorobutane–Sulfonyl Fluoride/1,8–Diazobicyclo[5.4.0]—undec–7–ene Into Their Corresponding Fluorides. *Tetrahedron Letters*, 36(15), 2611–2614 (1995).*

Hiroki Kumamoto et al., "Synthesis of 2–Alkynyl-cordycepins and Evaluation of Their Vasodilating Activity", Nucleosides & Nucleosides, vol. 17, No. 1–3, pp. 15–27, 1998.

Kirupa Shanmuganathan et al., "Enhanced Brain Delivery of An Anti–Hiv Nucleoside 2'–F–Ara–Ddi by Xanthine Oxidase Mediated Biotransformation", J. Med. Chem., vol. 37, pp. 821–827, 1994.

Tanya Koudriakova et al., "In Vitro and in Vivo Evaluation of 6–Azido–2', 3'–Dideoxy–2'–Fluoro–β–D–Arabinofuranosylpurine and $N^6$–Methyl–2', 3'–Dideoxy–2'–Fluoro–β–D–Arabinofuranosyladenine as Prodrugs of the Anti–HIV Nucleosides 2'–F—ARA–DDA and 2'–F–ARA–DDI", J. Med. Chem., vol. 39, pp. 4676–4681, 1996. (Issue No. 23).

(List continued on next page.)

*Primary Examiner*—Johann Richter
*Assistant Examiner*—Lawrence E. Crane
(74) *Attorney, Agent, or Firm*—Oblon, Spivak, McClelland, Maier & Neustadt, P.C.

(57) ABSTRACT

Novel intermediates of nucleoside derivatives, of which the 6-position of the nucleic acid base moiety is substituted with a halogen atom, are produced. Using those novel intermediates, even substrates, of which the 3'-position of the saccharide moiety is deoxylated, can be substituted at the 2'-position at an extremely high yield. Specifically, by subjecting a 3'-deoxy derivative of inosine to 6-halogenation to give a 6-halide of the derivative, and then subjecting it to 2'-deoxylation/substitution with a fluorine atom or the like, followed by further subjecting it to substitution with an amino group, a hydroxyl group or any other intended substituent at the 6-positioned halogen atom, nucleoside derivatives are produced at a high yield. Methods for producing nucleoside derivatives including 9-(2,3-dideoxy-2-fluoro-β-D-threo-pentofuranosyl)adenine (FddA) and their related compounds, in a simplified manner, at a high yield and at low costs, and especially Economical methods for substituting substrates, of which the 3'-position of the saccharide moiety is deoxylated, at the 2'-position to produce those nucleoside derivatives on an industrial scale are also provided.

13 Claims, No Drawings

OTHER PUBLICATIONS

Ronald J. Wysocki, Jr. et al., "A More Expedient Approach to the Synthesis of Anti–HIV–Active 2,3–Dideoxy–2–Fluoro–β–D–Threo–Pentofuranosyl Nucleosides", Synthesis, vol. 11, pp. 1005–1008, 1991. (Nov.).

Harry Ford, Jr. et al., "Lipophilic, Acid–Stable, Adenosine Deaminase–Activated Anti–HIV Prodrugs for Central Nervous System Delivery. 2. 6–Halo and 6–Alkoxy Prodrugs of 2'-β–Fluoro–2',3'–Dideoxyinosine", J. Med. Chem., vol. 38, pp. 1189–1195, 1995. (Issue No. 7).

* cited by examiner

METHODS FOR PRODUCING NUCLEOSIDE DERIVATIVES AND INTERMEDIATES THEREFOR

This application is a Continuation of U.S. application, Ser. No. 09/267,789, filed Mar. 15, 1999, now allowed, now U.S. Pat. No. 6,090,937.

BACKGROUND OF THE INVENTION

1. Field of the Invention

The present invention relates to a novel method for producing nucleoside derivatives, more precisely to a novel method for producing nucleoside derivatives including 9-(2, 3-dideoxy-2-fluoro-β-D-threo-pentofuranosyl)adenine (hereinafter referred to as "FddA") and its related compounds which are useful as anti-viral agents, to novel intermediates in the method, and to a novel method for producing the intermediates.

2. Description of the Related Art

It is reported that 9-(2,3-dideoxy-2-fluoro-β-D-threo-pentofuranosyl)adenine (FddA) has a strong anti-viral activity against human immunodeficiency virus (HIV) and is greatly effective for treatment of acquired immune deficiency syndrome (AIDS) (see V. E. Marquetz, et al., Biochem. Pharmacol., (36) page 2719, 1987; P. Herdewijn, et al., J. Med. Chem., (30), page 2131, 1987), and many clinical tests using it for the treatment of AIDS and AIDS-related complications (ARC) are being made at present. Recently, in addition, reported are FddA derivatives as modified at the nucleic acid base site to improve their potency (see C. K. Chu, et al., J.Med. Chem., (37), page 821, 1994; J. S. Driscoll, et al., J. Med. Chem., (39), page 1619, 1996; C. K. Chu, et al., J. Med. Chem., (39), page 4676, 1996).

The most direct method for producing FddA and its related compounds comprises substituting a substrate, of which the 3'-position in the saccharide moiety is deoxylated, at its 2'-position (see P. Herdewijn, et al., J. Med. Chem., (30), page 2131, 1987; V. E. Marquez, et al., J. Med. Chem., (33), page 978, 1990; H. Shiragami, et al., Nucleosides & Nucleotides, (11), page 391, 1992). However, the yield in the conventional methods is extremely low or is not higher than 10% and the reagent, diethylaminosulfer trifuluoride (DAST), is not available in industrial amount, and therefore the methods could not be used for industrial production of FddA and its related compounds.

1. Problems to be Solved by the Invention

In the course of the completion to the present invention, the above and following problems in the related art have been also found by the present inventors.

Given the situation as above, it is desired to develop an inexpensive method for producing nucleoside derivatives including 9-(2,3-dideoxy-2-fluoro-β-D-threo-pentofuranosyl)adenine (FddA) and its related compounds, in a simplified manner and at a high yield, in particular, an economical and industrial method for producing those nucleoside derivatives that comprises substituting a substrate, of which the 3'-position of the saccharide moiety is deoxylated, at its 2'-position at a high yield. Accordingly, the subject matter in the art is to provide such an excellent production method.

The object of the present invention is to develop an advantageous method for producing the nucleoside derivatives noted above, especially those having anti-viral activity, and to provide intermediates in the method and also a simple method for producing the intermediates.

SUMMARY OF THE INVENTION

We, the present inventors have assiduously studied in order to solve the problems noted above, and, as a result, have found, in a process for producing nucleoside derivatives including 9-(2,3-dideoxy-2-fluoro-β-D-threo-pentofuranosyl)adenine (FddA) and its related compounds, by subjecting a 3'-deoxy derivative of adenine to 2'-deoxylation/substitution with a flurine atom or the like (see P. herdewijn, et al., J. Med. Chem., (30), page 2131, 1987; V. E. Marquez, et al., J. Med. Chem., (33), page 978, 1990; H. Shiragami, et al., Nucleosides & Nucleotides, (11), page 391, 1992 ), the yield thereof is extremely low mainly due to a rearrangement of adenine base.

It is reported that, by subjecting a derivative of adenine, of which the 3'-position is not deoxylated, to 2'-deoxylation/substitution with a fluorine atom or the like, the same kind of rearrangement has occurred as side reaction and lowered the yield (see K. A. Watanabe, et al., J. Org. Chem., (57), page 553, 1992 ). Furthermore, it is reported that, by chlorination at the 6-position of the nucleic acid, this kind of rearrangement can be suppressed (see T. Maruyama, et al., Chem. Pharm. Bull., (44), page 2331, 1996). However, it is not known the case of 3'-deoxy derivatives.

Therefore, we, the present inventors have produced novel intermediates of a general formula (1) mentioned below, which are derivatives as deoxylated at the 3'-position and substituted by a halogen atom at the 6-position of the nucleic acid. Using those novel intermediates, we have found that even substrates, of which the 3'-position of the nucleic acid is deoxylated, can suppress the troblesome rearrangement completely and can be substituted at the 2'-position at an extremely high yield. On the basis of these findings, we have completed the present invention.

Specifically, by subjecting a 3'-deoxy derivative of inosine to 6-halogenation step for halogenating it at the 6-position thereof to give a 6-halide of the derivative, and then subjecting it to 2'-deoxylation/substitution with a fluorine atom or the like, followed by further subjecting it to substitution with an amino group, a hydroxyl group or any other intended substituent at the 6-positioned halogen atom, we have made it possible to produce the intended nucleoside derivatives.

On the basis of our findings noted above, hereinunder illustrated is one embodiment of the production route to give nucleoside derivatives, which covers all the steps in series as concretely demonstrated in Examples to be mentioned hereinafter. All those steps and the compounds as produced therein are usable in the process of producing nucleoside derivatives of the present invention. Naturally, the invention encompasses not only all the steps constituting this production route but also any and every method comprising any one of those steps, novel intermediates as produced in those steps and even the use of those novel intermediates, especially the use thereof for producing various nucleoside derivatives. Production Route:

Production Route

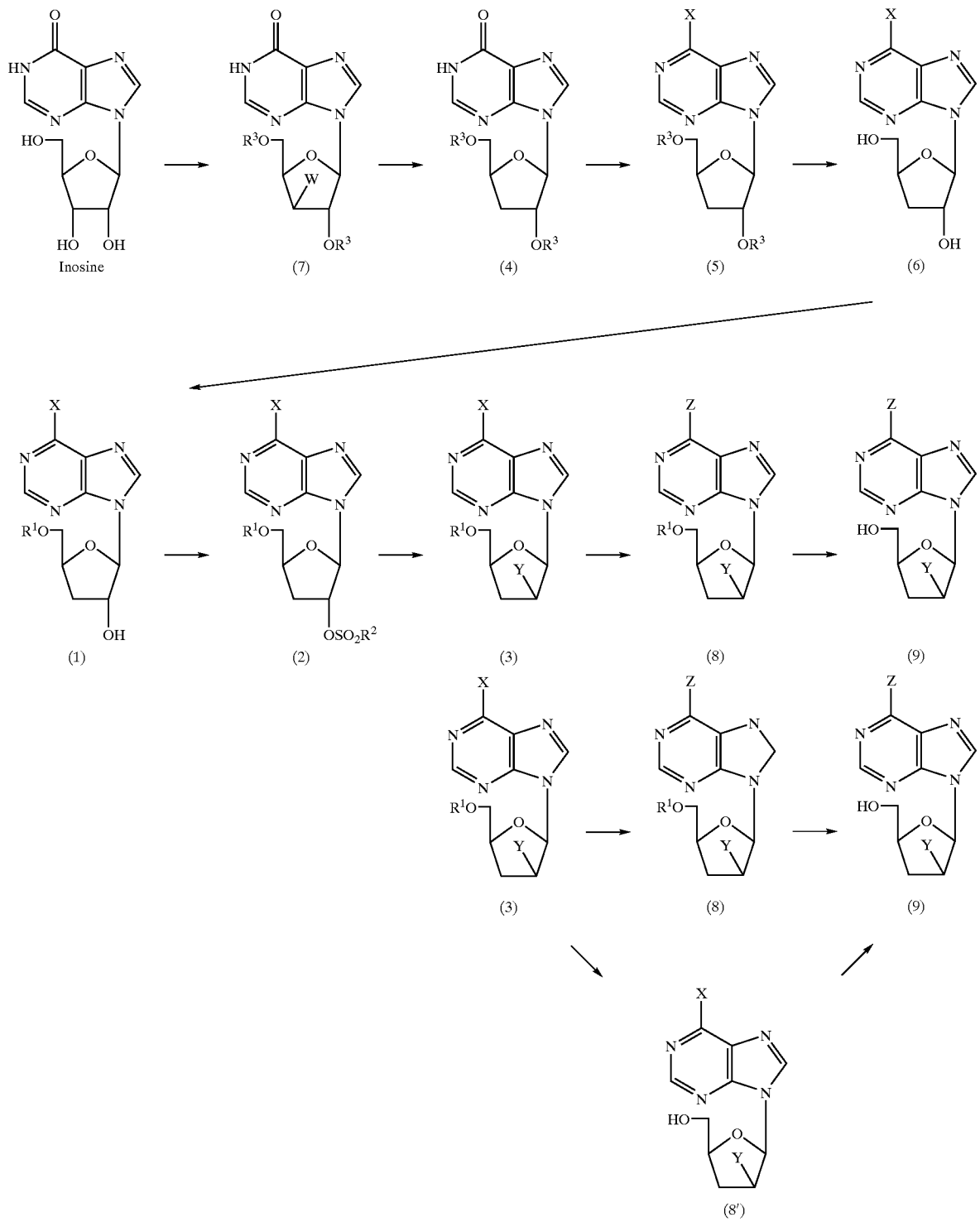

In those formulae, W represents a halogen atom, X represents a halogen atom, Y represents a substituent of any of a fluorine atom, an azido group or a cyano group, Z represents any one of a hydrogen atom, an amino group, a hydroxyl group, an azido group, a substituent of a formula $OR^4$, a substituent of a formula $SR^4$ and a substituent of a formula $NHR^4$, $R^1$ represents a protective group for the hydroxyl group, $SO_2R^2$ represents a sulfonic acid-type leaving group, $R^3$ represents a protective group for the hydroxyl group, and $R^4$ represents an optionally. phenyl-substituted, lower (e.g., C1–5) alkyl group.

Preferably, $R^2$ represents a halogen atom, an optionally-substituted aryl, alkyl or aralkyl group, or an optionally-substituted alkylamino group.

Regarding the definitions and the meanings of the compounds of general formula (1) to (9) as referred to herein, it shall be understood that the compounds designated by the same formula number are the same ones even though they are not individually described herein.

The invention encompasses a novel method for producing the nucleoside derivatives mentioned herein from the novel intermediates (1) and also from various raw compounds, novel intermediates including the intermediates (1) which are for producing the nucleotide derivatives, a novel method for producing those intermediates, and the use of the intermediates. More precisely, the present invention encompasses the following matters.

(i) A method for producing a nucleoside derivative represented by the following general formula (8) or (9), comprising subjecting a 3'-deoxy derivative of inosine, of which a part or all of the two hydroxyl groups may or may not be optionally protected, to 6-halogenation step for halogenating the compound at the 6-position thereof to give a 6-halide of the derivative, and then subjecting it, optionally after protecting its 5'-position, to 2'-deoxylation/Y-substitution reaction step followed by further subjecting it to Z-substitution reaction at its 6-halogen atom:

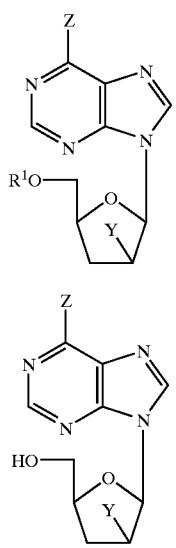

(8)

(9)

In the case of optionally protected 5'-position with a protective group in the derivative, the protective group may be de-protected in the suitable step, for example, before or after the Z-substitution reaction at its 6-halogen atom.

In such formula, as so mentioned hereinabove, Y represents a substituent of any one of a fluorine atom, an azido group and a cyano group, Z represents any one of a hydrogen atom, an amino group, a hydroxyl group, an azido group, a substituent of a formula $OR^4$, a substituent of a formula $SR^4$ and a substituent of a formula $NHR^4$, $R^1$ represents a protective group for the hydroxyl group, and $R^4$ represents an optionally phenyl-substituted, lower (e.g., C1–5) alkyl group.

The compound (8) obtained herein may be optionally subjected to deprotection at the 5'-position to convert them into 5'-deprotected derivative (9), as will be mentioned after.

On the other hand, the obtained compound (8') mentioned after may be optionally subjected to substitution with a group Z at its 6-halogen atom to give such derivative (9), as will be also mentioned after.

The nucleoside derivatives, compounds (9) in the present invention have anti-viral activity, in which Z is preferably a hydrogen atom, an amino group, a hydroxyl group, an azido group, a methylamino group, a methyloxy group or the like.

(ii) A method for producing a nucleoside derivative represented by the general formula (8) or (8') noted above, which comprises subjecting a compound represented by the following general formula (1) to 2'-deoxylation/Y-substitution reaction to give a compound represented by the following general formula (3);

and then subjecting the resulting compound (3) to substitution with a group Z at its 6-halogen atom to give the compound (8), or subjecting the compound (3) to deprotection at the 5'-position to convert the same into 5'-deprotected derivative (8').

One embodiment of the method comprises a step of processing the compound of formula (3), especially preferably that in which X is a chlorine atom and Y is a fluorine atom, to thereby substitute the substituent X with an amino group, preferably processing it in a solution of ammonia in an alcohol (e.g., methanol, ethanol, propanol, etc.), or a step of processing the compound to thereby substitute the substituent X with a hydroxyl group, preferably processing it in an aqueous solution of an alkali hydroxide (e.g., sodium hydroxide, potassium hydroxide, etc.), or a step of processing the compound to thereby substitute the substituent X with a hydrogen atom, preferably processing it with hydrogen in the presence of a reduction catalyst (e.g., palladium-carbon, Raney nickel, etc.), or a step of processing the compound to thereby substitute the substituent X with an azido group, preferably processing it with an alkali metal azide (e.g., sodium azide, lithium azide, etc.), to thereby produceng the nucleoside derivative of formula (8), and optionally comprises a step of deprotecting the resulting derivative at the protective group $R^1$ to obtain a nucleoside derivative represented by the following general formula (9).

Alternatively, the compound firstly (3) may be subjected to such above deprotecting step at the protective group $R^1$ to give the derivative (8'), and then the obtained this derivative (8') may be subjected to substitution with a group Z at its 6-halogen atom to give the compound (9) in the same manner as above.

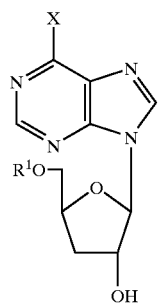

(1)

-continued

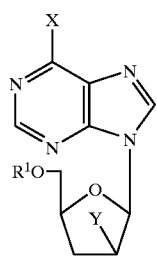

(3)

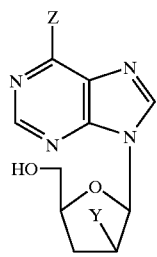

(9)

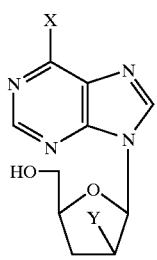

(8')

In those above formulae, as so mentioned hereinabove, X represents a halogen atom, Y represents a substituent of any one of a fluorine atom, an azido group and a cyano group, z represents any one of a hydrogen atom, an amino group, a hydroxyl group, an azido group, a substituent of a formula $OR^4$, a substituent of a formula $SR^4$ and a substituent of a formula $NHR^4$, $R^1$ represents a protective group for the hydroxyl group, and $R^4$ represents an optionally phenyl-substituted, lower (e.g., C1–5) alkyl group.

(iii) One embodiment of the method of (ii), wherein the reaction step includes a compound of the following formula (2) as the intermediate:

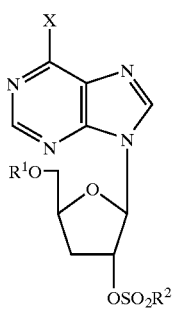

(2)

In this formula, as so mentioned hereinabove, X represents a halogen atom, $R^1$ represents a protective group for the hydroxyl group, and $SO_2R^2$ represents a sulfonic acid-type leaving group.

(iv) A method for producing compounds of formula (3) noted above, which comprise;

(a) subjecting a compound of formula (1) noted above to 2'-deoxylation/Y-substitution reaction step, preferably for removing the hydroxyl group from the compound followed by introducing a substituent Y, a fluorine atom, an azido group or a cyano group, thereinto, more preferably by reacting the compound with an alkylaminosulfur trifluoride reagent or a fluoroalkylamine reagent, or (b) subjecting a compound of formula (2) noted above to removal of 2'-leaving group/Y-substitution reaction step, or that is, processing the compound to thereby remove its O-sulfonic acid-type leaving group therefrom and introduce a substituent Y, a fluorine atom, an azido group or a cyano group, thereinto, preferably by reacting the compound with a reagent for attaining the substitution with a fluorine atom, an azido group or a cyano group, for example, reacting it with any one of azides, cyanides and fluorides, to thereby produce the intended compound (3).

In the meantime, the removal of 2'-leaving group in the present invention, the sulfonic acid-type leaving group is removed in the form of the O-sulfonic acid-type leaving group.

In these formulae, as so mentioned hereinabove, X represents a halogen atom, Y represents any one of a fluorine atom, an azido group and a cyano group, $R^1$ represents a protective group for the hydroxyl group, and $SO_2R^2$ represents a sulfonic acid-type leaving group. Preferably, $R^2$ represents a substituent of any one of a halogen atom, an aryl, alkyl and aralkyl group and also an alkylamino group, which may be optionally substituted (for example, with a halogen atom, etc.).

(v) Novel compounds of formulae (1) and (2) noted above, which are intermediates in the above-mentioned methods.

In those, X, Y, $R^1$ and $SO_2R^2$ have the same meanings as defined above.

(vi) One embodiment of the method (iv), in which the compound of formula (2) is prepared by reacting a compound of formula (1) noted above with a reagent for inserting a sulfonic acid-type leaving group thereinto, preferably by reacting it with a sulfonyl halide or a sulfonic acid anhydride, or reacting it with sulfuryl chloride and then with an amine or a halogens such as a fluorine or the like.

(vii) One embodiment of the method (i) or (ii), which comprises at least one of the following steps (A) to (E):

(A): a step of forming a compound of formula (3) according to the step (a) or (b) in the method (iv) noted above, (B): a step of dehalogenating a compound represented by the following general formula (7) to give a compound represented by the following general formula (4), (C): a step of reacting a compound represented by the following general formula (6) with a reagent for selectively protecting the 5'-position of the compound to give a compound of formula (1) noted above, (D): a step of subjecting a compound of formula (1) noted above to reaction of inserting a sulfonic acid-type leaving group thereinto, preferably by reacting the compound with a sulfonyl halide or a sulfonic acid anhydride, or reacting it with sulfuryl chloride and then with an amine or a halogen such as a fluorine or the like, to give a compound of the following general formula (2), and (E): a step of selectively halogenating a compound of the following general formula (4) at its 6-position with a halogenating agent to give a compound represented by the following general formula (5).

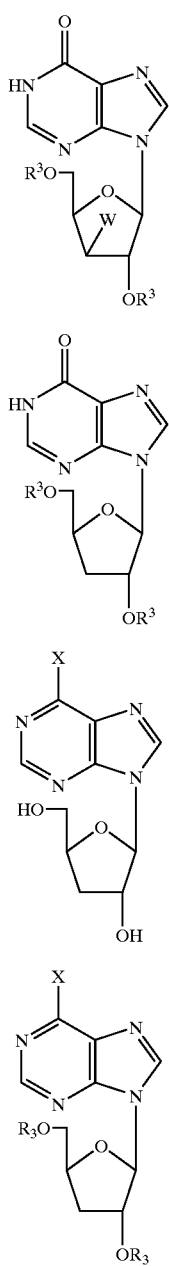

In those above formulae, as so mentioned hereinabove, X represents a halogen atom, Y represents a substituent of any one of a fluorine atom, an azido group and a cyano group, $R^1$ represents a protective group for the hydroxyl group, $SO_2R^2$ represents a sulfonic acid-type leaving group, in which $R^2$ is preferably a substituent of any of a halogen atom, and an aryl, alkyl or aralkyl group which may be optionally substituted (for example, with a halogen atom, etc.), and an alkylamino group which may be optionally substituted (for example, with a halogen atom, etc.), and $R^3$ represents a protective group for the hydroxyl group.

(viii) Novel compounds of formula (4) noted above, which are intermediates in the above-mentioned methods.

As so mentioned hereinabove, $R^3$ represents a protective group for the hydroxyl group.

(ix) A method for producing intermediates, which comprises at least any one of the steps (B) to (E).

This method for producing intermediates is usable in the method (vii) noted above. Apart from this, the method is also applicable to the production of other various useful compounds, as being simple and easy. Anyhow, this method is an excellent method for producing various intermediates.

In those formulae, as so mentioned hereinabove, X represents a halogen atom, Y represents a substituent of any one of a fluorine atom, an azido group and a cyano group, $R^1$ represents a protective group for the hydroxyl group, $SO_2R^2$ represents a sulfonic acid-type leaving group, in which $R^2$ is preferably a substituent of any one of a halogen atom, and an aryl, alkyl or aralkyl group which may be optionally substituted (for example, with a halogen atom, etc.), and also an alkylamino group which may be optionally substituted (for example, with a halogen atom, etc.), and $R^3$ represents a protective group for the hydroxyl group.

(x) Another embodiment of the method (i) or (ii) for producing nucleoside derivatives of the above-mentioned compounds (8), (8') or (9), in which is used any one in the intermediates covered in the (viii) noted above.

In this, as so mentioned hereinabove, X represents a halogen atom, Y represents a substituent of any one of a fluorine atom, an azido group and a cyano group, $R^1$ represents a protective group for the hydroxyl group, $SO_2R^2$ represents a sulfonic acid-type leaving group such as that mentioned above, in which $R^2$ is preferably a substituent of any one of a halogen atom, and an aryl, alkyl or aralkyl group which may be optionally substituted (for example, with a halogen atom, etc.), and also an alkylamino group which may be optionally substituted (for example, with a halogen atom, etc.), and $R^3$ represents a protective group for the hydroxyl group.

DETAILED DESCRIPTION OF THE PREFERRED EMBODIMENTS

Modes of carrying out the invention are described below.

Compounds of formula (7) noted above, such as typically 9-(2,5-di-O-acetyl-3-bromo-3-deoxy-β-D-xylofuranosyl) adenine, which are used in the invention, can be produced with ease in accordance with known methods (for example, see J. G. Moffatt, et al., J. Am. Chem. Soc., (95), page 4025, 1973). The substituent W is a halogen atom such as bromine.

The hydroxyl-protecting group, $R^3$ includes, for example, an acyl group (having from 1 to 10 carbon atoms), such as acetyl or benzoyl; an aralkyl group such as benzyl; and an alkyl group (having from 1 to 5 carbon atoms), such as allyl.

Compounds of formula (4) noted above for use in the invention can be obtained by de-halogenating the compounds of formula (7). To de-halogenate them, employable is any per-se known de-halogenating method, but preferred is a method of reducing the compound (7) with a radical reaction reagent, such as tri-n-butyl tin hydride, tris (trimethylsilyl)silane, diphenylsilane or diphenylmethylsilane in the presence of a radical reaction initiator such as azobisisobutyronitrile; or a method of reducing it with hydrogen in the presence of a reduction catalyst such as palladium-carbon or Raney nickel.

The compounds of formula (4) for use in the invention can also be obtained in any per-se known method (for example, a method for producing them from compounds of formula (7), such as that described by H. Shiragami et al., in Nucleosides & Nucleotides, (15), page 31, 1996). For example, 3'-deoxyinosine is prepared and any hydroxyl groups of the compound are protected to give the intended compound (4).

Compounds of formula (5) noted above for use in the invention have a halogen atom (e.g., chlorine) at the 6-position, and these are preferably obtained by halogenating a compound of formula (4) selectively at its 6-position with a halogenating agent. The halogenating agent includes, for example, a chlorinating agent of a combination of phosphorus oxychloride and N,N-dimethylaniline or a combination of sulfuryl chloride and dimethylformamide, and a chlorinating agent of dimethylchloromethyleneammonium chloride.

Compounds of formula (6) noted above for use in the invention can be obtained by de-protecting the compounds of formula (5). For the de-protection, preferably used is a mild method that may have no influence on the 6-halogen atom of the compounds (5). For example, compounds of formula (5) wherein X is a chlorine atom and $R^3$ is an acyl group, can be easily de-protected with ammonia or sodium methoxide as dissolved in an alcohol, such as methanol, without being influenced at the chlorine atom.

Compounds of formulae (5) and (6) noted above for use in the invention may be produced in per-se known methods (for example, see C. K. Chu et al., WO-9709052 (1997); Frederick William Hurry et al., Japanese Patent Kokoku Publication JP-B-42-17903), or that is, by coupling the nucleic acid base moiety and the saccharide moiety. In general, however, the known methods produce mixtures with unnecessary α-anomers, and therefore indispensably require the separation of the intended products from the mixtures. In addition, the yield of the intended products to be produced in the known methods is low. Therefore, the method of the invention that uses compounds (4) is preferred, as being easy and economical in industrial production of the compounds (5) and (6). The invention encompasses those compounds (4).

Compounds of formula (1) noted above, which the invention encompasses, can be produced by reacting the compound of formula (6) with a reagent capable of selectively protecting the 5'-position of the nucleosides.

In formula (1), $R^1$ is a protective group for the hydroxyl group, which may or may not be substituted (for example, with a halogen atom, an alkyl group having from 1 to 5 carbon atoms, an alkyloxy group having from 1 to 5 carbon atoms, etc.), and the protective group includes, for example, an acyl group such as acetyl or benzoyl; an alkyl group such as methoxymethyl or allyl; an aralkyl group such as benzyl or triphenylmethyl; a silyl group such as trimethylsilyl. As the reagent that gives such a protective group, for example, preferably used is any of an acylating agent, an alkylating agent, an aralkylating agent and an organic silylating agent. The acylating agent includes, for example, acid anhydrides such as acetic anhydride and benzoic anhydride, and acid halides such as acyl chloride and benzoyl chloride.

The alkylating agent includes, for example, alkyl halides such as chloromethyl methyl ether and allyl bromide. The aralkylating agent includes, for example, aralkyl halides such as benzyl bromide and triphenylmethyl chloride. The organic silylating agent includes, for example, organic silyl halides such as trimethylsilyl chloride. The reaction of the compound (6) with the protecting reagent is preferably effected in the presence of a base. The base usable in the reaction includes, for example, hydroxylamine, ammonia and their salts; primary to quaternary amines and their salts; metal hydroxides such as barium hydroxide; metal alkoxides such as sodium methoxide and potassium methoxide; lithium-ammonia solution; ion exchange resins; carbonates such as potassium carbonate, sodium carbonate and sodium hydrogencarbonate; phosphates such as disodium phosphate; acetates such as sodium acetate; and alkaline solutions of sodium hydroxide, lithium hydroxide or the like.

Regarding the reaction condition, the two may be reacted in a suitable solvent. As the solvent, preferably used is an organic solvent such as ethyl acetate, toluene, methylene chloride or methanol. The reaction solvent may be or may not be dewatered. Anyhow, after the reaction, the base, if used, in the reaction mixture is optionally neutralized, and the product formed can be isolated from the mixture through ordinary extraction using an organic solvent such as ethyl acetate, toluene or methylene chloride. Apart from this, the reaction mixture may be directly subjected to the next step without isolating the product therefrom.

Compounds of formula (1) wherein $R^3$ and $R^1$ are the same, for example, $R^3=R^1$=acetyl or benzoyl, may be obtained by de-protecting the compound of formula (5) selectively at the 2'-protective group.

Of compounds of formula (2) noted above, the hydrogen atom in the 2'-hydroxyl group is substituted with a sulfonic acid-type leaving group ($SO_2R^2$). In those, $R^2$ is preferably a substituent of any one of a halogen atom, and an aryl (having from 6 to 10 carbon atoms, such as phenyl), alkyl (having from 1 to 5 carbon atoms) or aralkyl (having from 7 to 19 carbon atoms, such as benzyl) group, which may or may not be substituted (for example, with a halogen atom, an alkyl group having from 1 to 5 carbon atoms, a nitro group, an alkyloxy group of which the alkyl moiety has from 1 to 5 carbon atoms, and the like), and also an alkylamino group (having from 1 to 6 carbon atoms), which may or may not be substituted (for example, with a halogen atom, an alkyl group having from 1 to 5 carbon atoms, a nitro group, an alkyloxy group of which the alkyl moiety has from 1 to 5 carbon atoms, and the like). More preferably, the protective group is any one of a chlorosulfonyl group, a fluorosulfonyl group, an imidazolesulfonyl group, a trifluoromethanesulfonyl group, a methanesulfonyl group, a an arylsulfonyl group such as a paratoluenesulfonyl, paranitrobenzenesulfonyl and benzenesulfonyl group, and the like.

Those compounds of formula (2) can be obtained by reacting the compound of formula (1) with a sulfonyl halide or a sulfonic acid anhydride, or by reacting it with sulfuryl chloride and then with an amine or a halogen. The sulfonyl halide includes, for example, arylsulfonyl halides such as paratoluenesulfonyl chloride and paranitrobenzenesulfonyl chloride; alkylsulfonyl halides such as methanesulfonyl chloride; aralkylsulfonyl halides such as benzylsulfonyl chloride; and halogenoalkylsulfonyl halides such as trifluoromethanesulfonyl chloride. The sulfonic acid anhydride includes, for example, arylsulfonic acid anhydrides such as paratoluenesulfonic acid anhydride and paranitrobenzenesulfonic acid anhydride; alkylsulfonic acid anhydrides such as methanesulfonic acid anhydride; aralkylsulfonic acid anhydrides such as benzylsulfonic acid anhydride; and halogenoalkylsulfonic acid anhydrides such as trifluoromethanesulfonic acid anhydride. The amine includes, for example, imidazole. The halogen includes, for example, fluorine.

The reaction to give compounds (2) may be effected in a suitable solvent. For this, preferably used is an organic solvent such as ethyl acetate, toluene or methylene chloride. The reaction may be effected in the presence of a basic catalyst such as pyridine, dimethylaminopyridine, triethylamine or the like. After the reaction, the basic catalyst, if used, in the reaction mixture is optionally neutralized, and the product formed can be isolated from the mixture through ordinary extraction using an organic solvent such as ethyl acetate, toluene and methylene chloride, And the like. Apart from this, the reaction mixture may be directly subjected to the next step without isolating the product therefrom.

In compounds of formula (3) noted above for use in the invention, Y is any one of a fluorine atom, an azido group and a cyano group. Those compounds (3) can be obtained by reacting the compound of formula (2) preferably with an azide, a cyanide or a fluoride. The azide includes, for example, alkali metal azides such as sodium azide and lithium azide; as well as ammonium azide and trimethylsilyl azide. The cyanide includes, for example, alkali metal cyanides such as sodium cyanide and lithium cyanide. The fluoride includes, for example, hydrogen fluoride; alkali metal fluorides such as lithium fluoride, potassium fluoride and cesium fluoride; alkylammonium fluorides such as tetrabutylammonium fluoride, pyridinium polyhydrogenfluoride and triethylamine trihydrofluoride; alkylaminosulfur trifluorides such as diethylaminosulfur trifluoride and morpholinosulfur trifluoride; and fluoroalkylamines such as Yarovenko reagent and Ishikawa reagent.

The reaction to give compounds (3) may be effected in a suitable solvent. For this, preferably used is an organic solvent such as ethyl acetate, toluene or methylene chloride. The reaction may be effected in the presence of a basic catalyst such as pyridine, dimethylaminopyridine or triethylamine. After the reaction, the basic catalyst, if used, in the reaction mixture is optionally neutralized, and the product formed can be isolated from the mixture through ordinary extraction using an organic solvent such as ethyl acetate, toluene or methylene chloride.

Compounds of formula (3) noted above for use in the invention, wherein Y is a fluorine atom, can be obtained by reacting the compound of formula (1) with a fluoride. The fluoride for this includes, for example, alkylaminosulfur trifluorides such as diethylaminosulfur trifluoride and morpholinosulfur trifluoride. This reaction may be effected in a suitable solvent. For this, preferably used is an organic solvent such as ethyl acetate, toluene and methylene chloride. The reaction may be effected in the presence of a basic catalyst such as pyridine, dimethylaminopyridine and triethylamine.

Compounds of formula (3) noted above for use in the invention, wherein X is a chlorine atom and Y is a fluorine atom, may be processed with ammonia as dissolved in methanol under pressure to thereby substitute X with an amino group, and thereafter the protective group $R^1$ in the resulting compounds may be de-protected in any suitable manner to give FddA. However, the usefulness of the compounds illustrated herein is not limited to this case.

To produce nucleoside derivatives of formula (8) noted above, for example, the compounds of formula (3) may be subjected to any of the following reaction steps.

To obtain the derivatives (8) wherein Z is an amino group, the compound (3) is processed with ammonia as dissolved in an alcohol such as methanol under pressure.

To obtain the derivatives (8) wherein Z is a hydroxyl group, the compound (3) is processed with an aqueous solution of an alkali hydroxide such as sodium hydroxide and potassium hydroxide.

To obtain the derivatives (8) wherein Z is a hydrogen atom, the compound (3) is processed with hydrogen in the presence of a reduction catalyst such as palladium-carbon.

To obtain the derivatives (8) wherein Z is an azido group, the compound (3) is processed with an alkali metal azide, such as sodium azide or lithium azide, in a solvent capable of dissolving the metal azide, such as dimethylformamide.

To obtain the derivatives (8) wherein Z is $OR^4$ or $SR^4$, the compound (3) is processed with a corresponding alkyl alcohol or alkyl thiol having been activated with an alkali metal halide such as a sodium halide.

To obtain the derivatives (8) wherein Z is $NHR^4$, the compound (3) is processed with an alkylamine (corresponding to the intended substituent, such as methylamine), preferably in an inert solvent such as dimethylformamide.

In formula (8), $R^4$ indicates an optionally phenyl-substituted lower (C1–5) alkyl group, such as a methyl, ethyl, propyl, butyl and benzyl group.

Nucleoside derivatives of formula (9) may be produced with ease by de-protecting the compounds of formula (8). For example, compounds (8) wherein $R^1$ is an acyl group such as an acetyl and benzoyl group may be processed with an alkali (e.g., sodium hydroxide, potassium hydroxide); those wherein $R^1$ is an alkyl group such as a methoxymethyl and allyl group may be processed with an acid such as hydrochloric acid and acetic acid; those wherein $R^1$ is an aralkyl group such as a benzyl or triphenylmethyl group may be processed with hydrogen in the presence of a reduction catalyst such as palladium-carbon and Raney nickel, or may be processed with an acid such as acetic acid; and those wherein $R^1$ is a silyl group such as a trimethylsilyl group may be processed with tetraammonium fluoride or the like, to thereby give the derivatives of formula (9).

Alternatively, the above mentioned de-protecting reaction step at the 5'-potion thereof may be conducted and then substitution reaction with Z group may be conducted. In this case,the compound (3) firstly may be subjected to such above deprotecting step at the protective group $R^1$ in the same manner as above to give the derivative (8'), and then thus obtained derivative (8') may be subjected to substitution with a group Z at its 6-halogen atom to give the compound (9) also in the same manner as above.

EXAMPLES

Now, the invention is described in detail with reference to the following Examples.

Example 1

Production of 9-(2,5-di-O-acetyl-3-bromo-3-deoxy-β-D-xylofuranosyl)-1,9-dihydro-6H-purine-6-one 400 g (1.49 mols) of inosine was suspended in 800 ml of acetic acid in a 2-liter glass reactor, to which was added 240 ml (1.92 mols) of trimethyl ortho-acetate, and reacted at 35° C. for 5 hours. The reaction mixture was concentrated under reduced pressure while acetic acid was added thereto, to thereby remove almost all methanol therefrom. The resulting concentrate was dissolved in 900 ml of acetonitrile added thereto, and cooled at 0° C., to which was dropwise and slowly added 280 ml (3.79 mols) of acetyl bromide over a period of about 5 hours. The resulting white slurry was dropwise added to 1.6 liters of a 1/1 mixture of water and acetonitrile that had been prepared separately, while being neutralized with an aqueous solution of 25% sodium hydroxide, whereby the reaction was stopped. The neutralizing rate was so adjusted that the pH value of the system might fall between 6.0 and 7.0 or so. For this neutralization, used was about 1.3 liters of the aqueous solution of 25% sodium hydroxide. To the resulting reaction mixture, added was 800 ml of acetonitrile to separate the organic layer and the aqueous layer. The aqueous layer was back-extracted with acetonitrile and ethyl acetate. The organic layers were combined and concentrated to have a desired volume, and then washed with a saturated saline solution and an aqueous saturated solution of sodium hydrogencarbonate, dried with anhydrous magnesium sulfate, and filtered. The solvent was evaporated out from the resulting filtrate, and a syrupy product was obtained. This was analyzed through liquid chromatography. The yield of the entitled compound was 53.8%.

¹H-NMR (300 MHz, CDCl₃) δ: 8.34 (1H, s, H2), 8.24 (1H, s, H8), 6.20 (1H, bs, H1') 5.74 (1H, bs, H2'), 4.4 to 4.6 (4H, m, H3', H4', H5'ab), 2.20 (3H, s, 5'OAc), 2.14 (3H, s, 2'OAc).

IR (KBr, cm⁻¹): 1750, 1698, 1376, 1226, 1043.

UV (MeOH) λmax: 206 (log ε 2.22), 245 (log ε 1.53) nm.

MS (ESI) m/z: 415, 417 (M+H)⁺, 829, 831, 833 (2M+H)⁺.

Example 2

Production of 2',5'-di-O-acetyl-3'-deoxyinosine 3.67 g (8.85 mmols) of 9-(2,5-di-O-acetyl-3-bromo-3-deoxy-β-D-xylofuranosyl)-1,9-dihydro-6H-purine-6-one was dissolved in 66 ml of toluene in a 200-ml reactor, to which were added 7.35 ml (26.5 mmols) of tributyl tin hydride and 125 mg (0.761 mmols) of 2,2'-azobisisobutyronitrile. The reaction mixture was heated up to 95° C. and reacted for 1 hour, and then cooled to 0° C., and then dropwise added to 35 ml of petroleum ether that had been prepared separately, to stop the reaction. The white precipitate thus formed was taken out through filtration, and recrystallized from 46 ml of ethanol and 35 ml of acetonitrile hydrate. The crystals were taken out through filtration and dried at 40° C. under reduced pressure to obtain 1.88 g (5.58 mmols, yield: 63.1%) of white crystals.

¹H-NMR (300 MHz, CDCl₃) δ: 8.08 (1H, s, H2), 8.07 (1H, s, H2), 6.04 (1H, d, J=1.1 Hz, H1'), 5.59 (1H, bd, J=5.9 Hz, H2'), 4.60 (1H, m, H4'), 4.39 (1H, dd, J=12.3, 2.9 Hz, H5'a), 4.22 (1H, dd, J=12.3, 5.2 Hz, H5'b), 2.50 (1H, ddd, J=14.0, 10.5, 5.9 Hz, H3'a), 2.16 (1H, ddd, J=14.0, 5.8, 1.1 Hz, H3'b), 2.09 (3H, s, 5'OAc), 2.04 (3H, s, 2'OAc).

¹H-NMR (300 MHz, DMSO-d6) δ: 8.26 (1H, s, H2), 8.10 (1H, s H8), 6.11 (1H, d, J=1.4 Hz, H1'), 5.61 (1H, bd, J=6.3 Hz, H2'), 4.52 (1H, m, H4'), 4.29 (1H, dd, J=12.0, 2.9 Hz, H5'a), 4.16 (1H, dd, J=12.0, 5.8 Hz, H5'b), 2.60 (1H, ddd, J=14.1, 10.3, 6.3 Hz, H3'a), 2.22 (1H, ddd, J=14.1, 5.9, 1.1 Hz, H3'b), 2.10 (3H, s, 5'OAc), 1.99 (3H, s, 2'OAc).

IR (KBr, cm⁻¹): 1746, 1724, 1707, 1419, 1344, 1230, 1205, 1122, 1100.

UV (MeOH) λmax: 203 (log ε 1.42), 245 (log ε 0.83) nm.

MS (ESI) m/z: 359 (M+Na)⁺, 695 (2M+Na)⁺.

Example 3

Production of 6-chloro-9-(2,5-di-O-acetyl-3-deoxy-β-D-erythro-pentofuranosyl)-9H-purine 32.7 g (97.2 mmols) of 2',5'-di-O-acetyl-3'-deoxyinosine was suspended in 449 ml of methylene chloride in a 1-liter reactor, to which were added 30.1 ml (389 mmols) of dimethylformamide and 28.0 ml (389 mmols) of thionyl chloride, and reacted for about 7 hours while heating under reflux. The reaction mixture was cooled to 0° C., and then dropwise added to 500 ml of water that had been cooled at 0° C. to stop the reaction. The reaction mixture was separated into layers, and the organic layer was taken out, and washed with water, an aqueous saturated solution of sodium hydrogencarbonate and a saturated saline solution in that order. The solvent was evaporated, and 31.0 g of an oily product was obtained. This crude product was directly subjected to the next reaction.

Example 4

Production of 6-chloro-9-(3-deoxy-β-D-erythro-pentofuranosyl)-9H-purine 31.0 g (83.4 mmols) of 6-chloro-9-(2,5-di-O-acetyl-3-deoxy-β-D-erythro-pentofuranosyl)-9H-purine was dissolved in 103 ml of methanol in a 500-ml reactor, and cooled to 0° C., to which was added 1.60 g (8.31 mmols) of 28% sodium methoxide. These were reacted at room temperature for 3 hours, and then cooled to 0° C. The crystals thus formed were taken out through filtration. These were washed with 18 ml of cold methanol, and then dried at 50° C. under reduced pressure to obtain 14.7 g of white crystals (purity 99.2%; 53.9 mmols; overall yield 55.4% [2 stages]).

¹H-NMR (300 MHz, CDCl₃) δ: 8.68 (1H, s, H2), 8.33 (1H, s, H8), 5.83 (1H, d, J=4.6 Hz, H1'), 4.92 (1H, ddd, J=7.2, 6.5, 4.6 Hz, H2'), 4.56 (1H, m, H4'), 3.98 (1H, dd, J=12.5, 2.1 Hz, H5'a), 3.60 (1H, dd, d=12.5, 2.6 Hz, H5'b), 2.53 (1H, ddd, J=12.9, 7.2, 5.7 Hz, H3'a), 2.18 (1H, ddd, J=12.9, 8.0, 6.5 Hz, H3'b).

¹H-NMR (300 MHz, DMSO-d6) δ: 8.97 (1H, s, H2), 8.82 (1H, s, H8), 6.06 (1H, d, J=1.4 Hz, H1'), 5.80 (1H, s, J=3.9 Hz, H2'—OH), 5.12 (1H, dd, J=5.3, 5.2 Hz, H5'—OH), 4.65 (1H, m, H2'), 4.46 (1H, m, H4'), 3.78 (1H, ddd, J=12.1, 5.3, 3.2 Hz, H5'a), 3.59 (1H, ddd, J=12.1, 5.2, 3.8 Hz, H5'b), 2.28 (1H, ddd, J=13.3, 9.6, 5.3 Hz, H3'a), 1.93 (1H, ddd, J=12.3, 6.0, 2.2 Hz, H3'b).

IR (KBr, cm⁻¹): 3331, 3105, 3074, 2938, 2920, 1596, 1562, 1492, 1442, 1426, 1405, 1391, 1337, 1207, 1129, 1079, 1068, 1002, 979, 834, 806, 635.

UV (MeOH) λmax: 204 (log ε 1.17), 265 (log ε 0.45) nm.

MS (ESI) m/z: 271 (M+H)⁺.

Example 5

Production of 6-chloro-9-[3-deoxy-5-O-(triphenylmethyl)-β-D-erythro-pentofuranosyl]-9H-purine 1.38 g (5.10 mmols) of 6-chloro-9-(3-deoxy-β-D-erythro-pentofuranosyl)-9H-purine was dissolved in 41 ml of dry dimethylformamide, to which were added 2.3 ml (16.5 mmols) of triethylamine and 0.424 g (3.47 mmols) of 4-dimethylaminopyridine. Then, 4.79 g (16.8 mmols) of trityl chloride was added thereto, and these were reacted for about 16.5 hours at 50° C. After having been cooled, 8 ml of water was added to the reaction mixture, and the solvent was evaporated therefrom. The removal of the solvent was repeated four times. The residue was dissolved in 100 ml of methylene chloride and 50 ml of water. After having been thus separated, the organic layer was washed four times with 50 ml of water each, dried with anhydrous sodium sulfate, and then filtered. The resulting filtrate was applied to a silica gel column (silica: 100 g), and eluted with methylene chloride and then with 1 to 10% methanol/methylene chloride solutions. The solvent was evaporated to obtain 2.71 g of an oily product (purity 85.3%; yield 88.5%).

¹H-NMR (300 MHz, CDCl₃) δ: 8.64 (1H, s, H2), 8.40 (1H, s H8), 7.41 to 7.21 (15H, m, 5'OTr), 6.04 (1H, d, J=2.2 Hz, H1'), 4.87 (1H, m, H2'), 4.73 (1H, m, H4'), 3.44 (1H, dd, J=10.6, 3.1 Hz, H5'a), 3.33 (1H, dd, J=10.6, 4.6 Hz, H5'b), 2.30 (1H, ddd, J=13,3. 7.7, 5.6 Hz, H3'a), 2.17 (1H, ddd, J=13.3, 6.5, 3.9 Hz, H3'b).

IR (KBr, cm⁻¹): 3354, 3059, 1592, 1562, 1491, 1449, 1400, 1338, 1206, 1130, 1078, 1018, 952, 766, 748, 704, 634.

UV (MeOH) λmax: 207 (log ε 2.27), 265 (log ε 0.31) nm.

MS (ESI) m/z: 513 (M+H)⁺.

Example 6

Production of 6-chloro-9-[2,3-dideoxy-2-fluoro-5-O-(triphenylmethyl)-β-D-threo-pentofuranosyl]-9H-purine, Part 1

104 mg (0.202 mmols) of 6-chloro-9-[3-deoxy-5-O-(triphenylmethyl)-β-D-erythro-pentofuranosyl]-9H-purine, purine was dissolved in 10 ml of methylene chloride in a 30-ml reactor, to which was added 0.12 ml (1.48 mmols) of pyridine. This mixture was cooled to 0° C., to which was dropwise added 0.07 ml (0.530 mmols) of diethylaminosulfur trifluoride with stirring. Next, this was restored to be at room temperature, and then heated under reflux or about 4 hours. After having been again restored to be at room temperature, this was dropped into a mixture of 20 ml of an aqueous saturated solution of sodium hydrogencarbonate and 10 ml of methylene chloride with vigorously stirring, and then further stirred for about 20 minutes. The reaction mixture was separated into layers, and the organic layer was concentrated azeotropically with toluene. The residue was taken out and purified through a silica gel plate (using 50% hexane/ethyl acetate). The fraction of the intended product was extracted with ethyl acetate, and the solvent was evaporated to obtain 44.3 mg (yield 42.6%) of the objective compound, which was white solid.

$^1$H-NMR (300 MHz, CDCl$_3$) δ: 8.73 (1H, s, H2), 8.34 (1H, d, J=2.8 Hz, H8), 7.52 to 7.22 (15H, m, 5'OTr), 6.41 (1H, dd, J=19.1, 3.1 Hz, H1'), 5.25 (1H, dddd, J=53.7, 5.2, 3.1, 2.0 Hz, H2'), 4.46 (1H, m, H4'), 3.48 (1H, dd, J=9.9, 6.6 Hz, H5'a), 3.30 (1H, dd, J=9.9, 3.8 Hz, H5'b), 2.57 (1H, dddd, H=35.0, 14.8, 9.0, 5.6 Hz, H3'a), 2.36 (1H, dddd, J=27.5, 15.1, 5.1, 1.7 Hz, H3'b).

IR (KBr, cm$^{-1}$): 1593, 1567, 1492, 1220, 1206, 1079, 708.
UV (MeOH) λmax: 204 (log ε 1.17), 265 (log ε 0.45) nm.
MS (ESI) m/z: 515 (M+H)$^+$.

Example 7

Production of 6-chloro-9-[2-O-(sulfurylimidazolyl)-3-deoxy-5-O-(triphenylmethyl)-β-D-erythro-pentofuranosyl]-9H-purine 604 mg (1.18 mmols) of 6-chloro-9-[3-deoxy-5-O-(triphenylmethyl)-β-D-erythro-pentofuranosyl]-9H-purine was dissolved in 11.8 ml of methylene chloride, to which was added 486 mg (7.07 mmols) of imidazole. This reaction mixture was cooled to −35° C., to which was added 0.15 ml (1.77 mmols) of sulfuryl chloride, and stirred for 30 minutes. Then, after having been restored to be at room temperature, this was stirred overnight. To the reaction mixture, water was added to stop the reaction. Then, the mixture was separated into layers, and the aqueous layer was washed with dichloromethane. The organic layers were combined together, dried with anhydrous sodium sulfate, and filtered. The solvent was evaporated from the resulting filtrate. The residue was purified through silica gel column (silica 40 g), using 33 to 50% hexane/ethyl acetate, to obtain 570 mg (yield 75.0%) of the intended product, which was colorless oil.

$^1$H-NMR (300 MHz, CDCl$_3$) δ: 8.67 (1H, s, H2), 8.25 (1H, s, H8), 8.03 (1H, s, imidazole), 7.37 to 7.24 (16H, m, 5'OTr+imidazole), 7.16 (1H, s, imidazole), 6.11 (1H, s, H1'), 5.93 (1H, d, J=5.3 Hz, H2'), 4.65 (1H, m, H4'), 3.46 (1H, dd, J=10.8, 3.2 Hz, H5'a), 3.35 (1H, dd, J=10.8, 4.5 Hz, H5'b), 2.61 (1H, ddd, J=14.6, 9.7, 5.3 Hz, H3'a), 2.27 (1H, ddd, J=14.6, 5.7, 1.6 Hz, H3'b).

Example 8

Production of 6-chloro-9-[2,3-dideoxy-2-fluoro-5-O-(triphenylmethyl)-β-D-threo-pentofuranosyl]-9H-purine, Part 2

113 mg (0.176 mmols) of 6-chloro-9-[2-O-(sulfurylimidazolyl)-3-deoxy-5-O-(triphenylmethyl)-β-D-erythro-pentofuranosyl]-9H-purine was dissolved in 1.80 ml of toluene, to which was added 0.18 ml (1.06 mmols) of triethylamine trihydrofluoride, and stirred overnight at 50° C. After having been cooled, 10.0 ml of ethyl acetate and 8.0 ml of an aqueous saturated solution of sodium hydrogencarbonate were added to this, to separate it into layers. The organic layer was dried with anhydrous sodium sulfate, and filtered. Then, the solvent was evaporated from the filtrate. The residue was dissolved in acetonitrile and analyzed through liquid chromatography. The intended product was obtained at an yield of 41.9%.

Example 9

Production of 6-chloro-9-[2-O-(trifluoromethanesulfonyl)-3-deoxy-5-O-(triphenylmethyl)-β-D-erythro-pentofuranosyl]-9H-purine 164 mg (0.320 mmols) of 6-chloro-9-[3-deoxy-5-O-(triphenylmethyl)-β-D-erythro-pentofuranosyl]-9H-purine was dissolved in 9 ml of methylene chloride, to which was added 253 mg (3.20 mmols) of pyridine. To this mixture, dropwise added was a mixture of 361 ml of trifluoromethanesulfonic acid anhydride and 2 ml of methylene chloride at room temperature, and the resulting mixture was then stirred at room temperature for about 15 minutes. To the reaction mixture was added a mixture of 20 ml of an aqueous saturated solution of ammonium chloride and 10 ml of methylene chloride, by which the reaction was stopped. The organic layer separated was taken out, and then washed with an aqueous saturated solution of ammonium chloride, an aqueous saturated solution of sodium hydrogencarbonate and a saturated saline in that order. Then, the thus-washed organic layer was dried with anhydrous magnesium sulfate, and filtered. The solvent was evaporated out from the filtrate to obtain a white foamy solid. Analyzing this through high-performance liquid chromatography (HPLC) verified that the solid obtained was nearly a single substance. This solid was directly subjected to the next reaction step.

Example 10

Production of 6-chloro-9-[2,3-dideoxy-2-fluoro-5-O-(triphenylmethyl)-β-D-threo-pentofuranosyl]-9H-purine, Part 3

22.9 mg (0.0356 mmols) of 6-chloro-9-[2-O-(trifluoromethanesulfonyl)-3-deoxy-5-O-(triphenylmethyl)-β-D-erythro-pentofuranosyl]-9H-purine was dissolved in 2.0 ml of toluene, to which were added 10.8 mg (0.107 mmols) of triethylamine and 34.5 mg (0.214 mmols) of triethylamine trihydrofluoride, and stirred at room temperature for about 5 days. After having been cooled, all the mixture was dissolved in methanol, and analyzed through liquid chromatography. The intended product was obtained at an yield of 57.8%.

Example 11

Production of 9-[2,3-dideoxy-2-fluoro-5-O-(triphenylmethyl)-β-D-threo-pentofuranosyl]-9H-purine-6-amine 110 mg (0.214 mmols) of 6-chloro-9-[2,3-dideoxy-2-fluoro-5-O-(triphenylmethyl)-β-D-threo-pentofuranosyl]-9H-purine was dissolved in 17.2 ml of a solution of 20% ammonia/methanol, and kept overnight in a closed vessel at 60° C. After having been cooled, the reaction mixture was concentrated, and then distilled azeotropically with toluene. The crystals formed were taken out through filtration. These were dried at room temperature under reduced pressure to obtain 82.3 mg of a white solid (purity 74.4%; yield 57.7%).

$^1$H-NMR (300 MHz, CDCl$_3$) δ: 8.33 (1H, s, H2), 8.06 (1H, d, J=3.0 Hz, H8), 7.52 to 7.20 (15H, m, 5'OTr), 6.33 (1H, dd, J=19.9, 2.9 Hz, H1'), 6.18 (2H, bs, 6-NH2), 5.20 (1H, md, J=53.8 Hz, H2'), 4.40 (1H, m, H4'), 3.46 (1H, dd, J=10.0, 6.5 Hz, H5'a), 3.27 (1H, dd, J=10.0, 4.1 Hz, H5'b), 2.50 (1H, dddd, J=35.5, 14.9, 9.0, 5.4 Hz, H3'a), 2.31 (1H, dddd, J=27.5, 14.9, 4.8, 1.4 Hz, H3'b).

IR (KBr, cm$^{-1}$): 3151, 1649, 1599, 1578, 1403, 1063, 703
UV (MeOH) λmax: 208 (log ε 2.19), 259 (log ε 0.58) nm.
MS (ESI) m/z: 496 (M+H)$^+$.

Example 12

Production of 9-(2,3-dideoxy-2-fluoro-β-D-threo-pentofuranosyl)-9H-purine-6-amine 35.3 mg (0.0710 mmols) of 9-[2,3-dideoxy-2-fluoro-5-O-(triphenylmethyl)-β-D-threo-pentofuranosyl]-9H-purine-6-amine was dissolved in 1.0 ml of acetic acid, and stirred at room temperature for about 4 hours and then at 80° C. for about 3 hours. To this was added 1.0 ml of acetic acid, and cooled to room temperature. This was concentrated, and the residue formed was taken out and purified through a silica gel plate (using 91% methylene chloride/ethanol). The fraction of the intended product was extracted with methanol, and the solvent was evaporated out to obtain 11.1 mg (yield 61.5%) of the product which was white solid. The physical data of the product obtained herein were the same as those disclosed in the literature.

Example 13

Production of 6-chloro-9-[2-azido-2,3-dideoxy-5-O-(triphenylmethyl)-β-D-threo-pentofuranosyl]-9H-purine 1.0 g (1.95 mmols) of 6-chloro-9-[3-deoxy-5-O-(triphenylmethyl)-β-D-erythro-pentofuranosyl]-9H-purine was dissolved in 20 ml of methylene chloride. This mixture was cooled to 0° C., to which was added 0.47 ml (5.85 mmols) of pyridine. To this mixture, dropwise was added 0.66 ml (3.90 mmols) of trifluoromethanesulfonic acid anhydride, and the resulting mixture was then stirred at room temperature for about 1 hour. To the reaction mixture was added a mixture of 20 ml of an aqueous saturated solution of sodium hydrogencarbonate and 20 ml of methylene chloride, by which the reaction was stopped. The organic layer thus separated was taken out, and then washed with water. Then, the thus-washed organic layer was dried with anhydrous sodium sulfate, and filtered. The solvent was evaporated out from the filtrate to obtain an oily material. This oily material was dissolved in 10 ml of toluene and the solvent was evaporated out from the mixture to obtain a white foamy solid. This solid was directly subjected to the next step.

1.473 g of this solid was dissolved in 20 ml of dry dimethylformamide. This mixture was cooled to 0° C., to which was added 126.8 mg (1.95 mmols) of sodium azide, and stirred at room temperature for 1.5 hours. To the reaction mixture was added a mixture of 100 ml of methylene chloride and 70 ml of water having two phases, by which the reaction was stopped. The organic layer and the aqueous layer were separated. The aqueous layer was back extracted with a mixture of 100 ml of ethyl acetate and 100 ml of a saturated saline. The organic layers were combined together, dried with anhydrous sodium sulfate and filtered. The solvent was evaporated from the resulting filtrate. The residue was purified through silica gel column (silica gel 80 g), using 30 to 80% ethyl acetate/hexane, to obtain 0.84 g (yield 80%) of the intended product.

1H-NMR(300 MHz,CDCl3) δ: 8.72 (s,1H,H8), 8.37 (s,1,H2),7.20–7.54 (m,15H,Tr),6.43 (d,J=5.4 Hz,1H,H1'),4.54 (m,1H,H2'),4.40 (m,1H,H4'),3.50 (dd,J=10.4,5.5 Hz,1H, H5'a),3.41 (dd,J=10.4,4.0 Hz,1H,H5'b),2.20–2.59 (m,2H, H3').

MS(ESI)m/z:538 (M+H)$^+$.

Example 14

Production of 9-(2,3-dideoxy-2-fluoro-β-D-threo-pentofuranosyl)-9H-purine-6-amine (FddA), Part 2

3.65 g (7.09 mmols) of 6-chloro-9-[2,3-dideoxy-2-fluoro-5-O-(tripenylmethyl-β-D-threo-pentofuranosyl]-9H-purine was dissolved in 18 ml of methanol and 18 ml of toluene which is containing 0.5 equivalent of hydrogen chloride. This mixture was stirred at room temperature for about 4 hours. This was treated with 2 equivalents of poly (4-vinylpyridine), and filtered. The solvent was evaporated out from the filtrate under the reduced pressure. The residue was dissolved in 200 ml of methanol and 200 ml of toluene.

The mixture was kept under 3.5 bar of ammonia pressure in a closed vessel at 40 to 60° C. for 5 days. After having been cooled, the reaction mixture was concentrated, and added 80% acetone water solution. The crystals thus formed were taken out through filtration. These were dried and analyzed through liquid chromatography. The intended product, FddA, was obtained at an yield of 73% in two steps.

Effects of the Invention

According to the present invention, substrates of which the 3'-position of the saccharide moiety is deoxylated can be substituted at the 2'-position at a high yield to give nucleoside derivatives. Therefore, using the method of the invention, nucleoside derivatives including 9-(2,3-dideoxy-2-fluoro-β-D-threo-pentofuranosyl)adenine (FddA) and their related compounds can be produced in a simplified manner at a high yield. Accordingly, the method of the invention gives those nucleoside derivatives at low costs.

What is claimed is:

1. A method for producing a nucleoside derivative represented by formula (8) or (9):

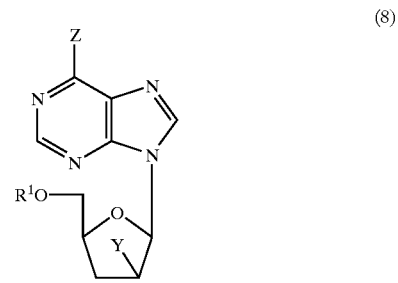

-continued (9)

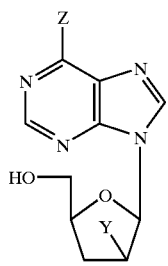

wherein
Y represents a fluorine atom, an azido group or a cyano group;
Z represents a hydrogen atom, an amino group, a hydroxyl group, an azido group, a substituent represented by formula $OR^4$, a substituent represented by formula $SR^4$ or a substituent represented by formula $NHR^4$;
$R^1$ represents hydroxyl protecting group; and
$R^4$ represents a lower alkyl group which is optionally substituted with one or more phenyl groups, comprising:
reacting a 3'-deoxy derivative of inosine represented by formula (4),
wherein $R^3$ represents a protective group for the hydroxyl group, with a halogenating agent to produce the corresponding 6-halo derivative of inosine represented by formula (5), (5)

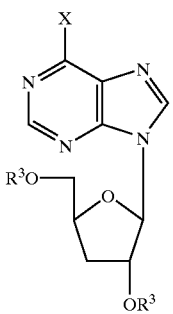

removing the 2' protecting group and the 5'-protecting group from the compound of formula (5) to produce the compound of formula (6):

(6)

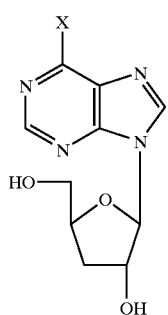

and selectively protecting the 5'-hydroxyl of the compound of formula (6) with an $R^1$ group wherein $R^1$ represents a hydroxyl protecting group and X represents a halogen atom, to produce the compound of formula (1), converting the 2'-hydroxyl group of the 6-halo derivative of inosine represented by formula (1) to an O-leaving group;
displacing the O-leaving group with a nucleophile selected from the group consisting of a fluoride ion, an azide ion and a cyanide ion; and then
substituting the halogen atom at the 6-position of the inosine derivative with a substituent selected from the group consisting of a hydrogen atom, an amino group, a hydroxyl group, an azido group, a substituent represented by formula $OR^4$, a substituent represented by formula $SR^4$ and a substituent represented by formula $NHR^4$, wherein $R^4$ is as defined above,
wherein said 6-halo derivative represented by formula (1) is optionally reacted with diethylaminosulfur trifluoride to produce the corresponding 2'-fluoro derivative, and then subjected to said substituting at the 6-position thereof.

2. The method of claim 1, wherein said converting the 2'-hydroxyl group of a compound represented by formula (1) to a leaving group produces a compound represented by formula (2):

(2)

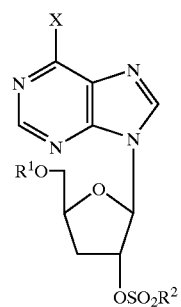

wherein
X represents a halogen atom;
$R^1$ represents a hydroxyl protecting group;
$O—SO_2R^2$ represents a sulfonic acid-type leaving group.

3. The method of claim 1, wherein Y is a fluorine atom.
4. The method of claim 1, wherein Z is an amino group.
5. The method of claim 1, further comprising:
removing the $R^1$ protecting group from the compound represented by formula (8) to provide a compound represented by formula (9):

(9)

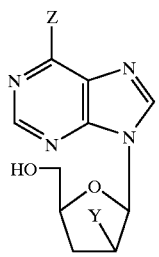

wherein Y and Z are as defined in claim 1.
6. A method of producing a compound represented by formula (4), comprising:
dehalogenating a compound represented by formula (7) to provide the compound represented by formula (4);

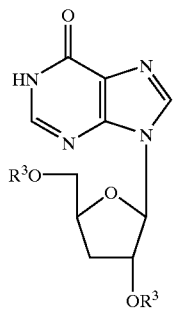

(4)

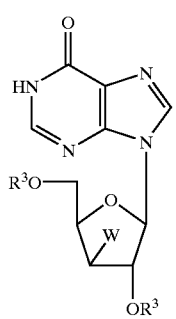

(7)

wherein

W represents a halogen atom; and
R³ represents a hydroxyl protecting group.

7. A method of producing the compound represented by formula (1), comprising:

producing the compound represented by formula (4) according to claim 6;

reacting the compound represented by formula (4) with a halogenating agent to produce the corresponding 6-halo derivative represented by formula (5); and removing the R³ groups of the 6-halo derivative represented by formula (5) to produce the compound represented by formula (6); and selectively protecting the 5' hydroxyl group of the compound represented by formula (6) with a R¹ group,

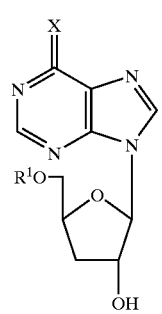

(1)

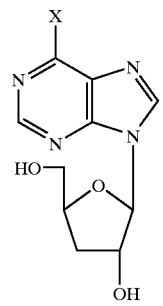

(6)

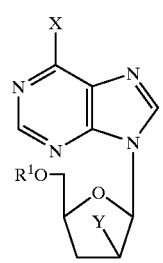

(5)

wherein

R¹ represents a hydroxyl protecting group;
R³ represents a hydroxyl protecting group; and
X represents a halogen atom.

8. A method of producing a compound represented by formula (3):

wherein

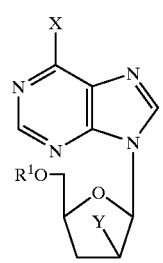

(3)

X represents a halogen atom;
Y represents a fluorine atom; and
R¹ represents a hydroxyl protecting group, comprising:

converting the 2'-hydroxyl group of a compound represented by formula (1) to an O-leaving group:

and displacing the O-leaving group with a fluoride ion to produce the compound

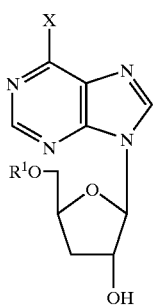

(1)

represented by formula (3); or reacting a compound represented by formula (1) with diethylaminosulfur trifluoride to produce a compound represented by formula (3).

9. A method of producing a compound represented by formula (8'):

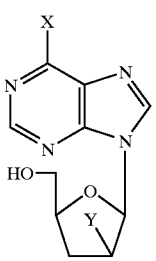

(8')

wherein
X represents a halogen atom; and
Y represents a fluorine atom, an azido group or a cyano group; comprising:
producing the compound represented by formula (3) according to claim 8; and
removing the $R^1$ protecting group from the compound represented by formula (3), to produce the compound represented by formula (8').

10. A method of producing a compound represented by formula (9):

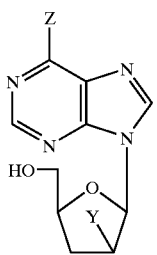

(9)

wherein
Y represents a fluorine atom, an azido group or a cyano group; and
Z represents a hydrogen atom, an amino group, a hydroxyl group, an azido group, a substituent represented by formula $OR^4$, a substituent represented by formula $SR^4$ or a substituent represented by formula $NHR^4$; and $R^4$ represents a lower alkyl group which is optionally substituted with one or more phenyl groups, further comprising:
producing the compound represented by formula (3) according to claim 8; and
substituting the halogen atom at the 6-position of the compound of formula (3) with a substituent selected from the group consisting of a hydrogen atom, an amino group, a hydroxyl group, an azido group, a substituent represented by formula $NHR^4$, a substituent represented by formula $OR^4$, and a substituent represented by formula $SR^4$ to produce the compound represented by formula (8), or
removing the protecting group $R^1$ from the compound of formula (3), to provide the compound represented by formula (8'),

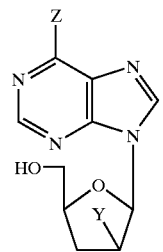

(8)

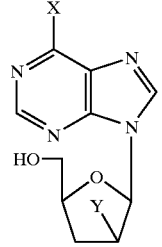

(8')

wherein
X represents a halogen atom;
Y represents a fluorine atom, an azido group or a cyano group;
Z represents a hydrogen atom, an amino group, a hydroxyl group, an azido group, a substituent represented by formula $OR^4$, a substituent represented by formula $SR^4$ or a substituent represented by formula $NHR^4$; and
substituting the halogen atom at the 6-position of the compound of formula (8') with a substituent selected from the group consisting of a hydrogen atom, an amino group, a hydroxyl group, an azido group, a substituent represented by formula $OR^4$, a substituent represented by formula $SR^4$ and a substituent represented by formula $NHR^4$; or
removing the $R^1$ protecting group from the compound of formula (8) to produce the compound represented by formula (9).

11. A method of producing a compound represented by formula (3):

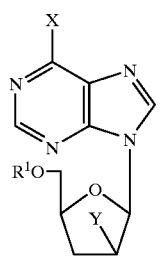

(3)

wherein
X represents a halogen atom;
Y represents a fluorine atom, an azido group or a cyano group; and
R$^1$ represents a hydroxyl protecting group, comprising:
converting the 2' hydroxyl group of a compound represented by formula (1) to an O-leaving group:

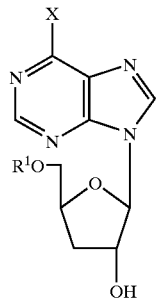

(1)

and displacing the O-leaving group with a fluoride, azide or cyanide ion to produce the compound represented by formula (3).

12. A method of producing a compound represented by formula (8'):

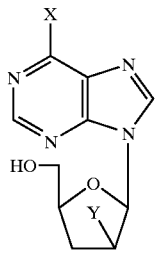

(8')

wherein

X represents a halogen atom; and
Y represents a fluorine atom, an azido group or a cyano group; comprising:
producing the compound represented by formula (3) according to the method of claim 11; and
removing the R$^1$ group, to produce the compound represented by formula (8').

13. A method of producing a compound represented by formula (9):

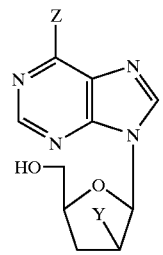

(9)

wherein

Y represents a fluorine atom, an azido group or a cyano group; and
Z represents a hydrogen atom, an amino group, a hydroxyl group, an azido group, a substituent represented by formula OR$^4$, a substituent represented by formula SR$^4$ or a substituent represented by formula NHR$^4$; and
R$^4$ represents a lower alkyl group which is optionally substituted with one or more phenyl groups comprising:
producing the compound represented by formula (8') according to the method of claim 12; and
substituting the halogen atom at the 6 position with a substituent selected from the group consisting of a hydrogen atom, an amino group, a hydroxyl group, an azido group, a substituent represented by formula OR$^4$, a substituent represented by formula SR$^4$ and a substituent represented by formula NHR$^4$, wherein R$^4$ is defined above, to produce the compound represented by formula (9).

* * * * *